United States Patent
Thompson et al.

(10) Patent No.: US 12,263,232 B1
(45) Date of Patent: Apr. 1, 2025

(54) COMPOSITION FOR REGULATING PRODUCTION OF PROTEINS

(71) Applicant: Wyvern Pharmaceuticals Inc., Calgary (CA)

(72) Inventors: Jill L. Thompson, Calgary (CA); Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/739,091

(22) Filed: Jun. 10, 2024

(51) Int. Cl.
- *A61K 48/00* (2006.01)
- *A61K 38/17* (2006.01)
- *C12N 15/86* (2006.01)

(52) U.S. Cl.
CPC ........ *A61K 48/005* (2013.01); *A61K 38/1774* (2013.01); *C12N 15/86* (2013.01); *C12N 2750/14143* (2013.01)

(58) Field of Classification Search
CPC .. A61K 48/005; A61K 38/1774; C12N 15/86; C12N 2750/14143
See application file for complete search history.

(56) References Cited

U.S. PATENT DOCUMENTS

| | | | | |
|---|---|---|---|---|
| 11,603,541 | B2 * | 3/2023 | Thompson | C12N 15/86 |
| 11,873,505 | B2 * | 1/2024 | Thompson | C12N 15/86 |
| 2020/0368369 | A1 * | 11/2020 | Thompson | A61K 35/15 |
| 2022/0251208 | A1 * | 8/2022 | Morsey | C07K 16/2818 |
| 2023/0340533 | A1 * | 10/2023 | Thompson | A61P 35/00 |

OTHER PUBLICATIONS

Teng (et al. 2023. PAD2: A potential target for tumor therapy. BBA-Rev. Cancer 1878:188931) (Year: 2023).*
Rouf (et al. 2023. The recent advances and future perspectives of genetic compensation studies in the zebrafish model. Genes & Diseases 10:468-479) (Year: 2023).*
Wikipedia (2024. Post translational modification. Available online at: en.wikipedia.org/wiki/Post-translational_modification. Accessed on Sep. 10, 2024) (Year: 2024).*
Wikipedia (2024. Expression vector. Available online at en.wikipedia.org. Accessed on Sep. 10, 2024) (Year: 2024).*
American Society of Gene & Cell Therapy (2024. Vectors 101. Available online at asgct.org. Accessed on Sep. 11, 2024) (Year: 2024).*
Wikipedia-Virus (2024. Group of pages: Flavivirus; Rotavirus; Dependoparvovirus; and Orthopoxvirus. Available online at en.wikipedia.org. Accessed on Sep. 10, 2024) (Year: 2024).*

* cited by examiner

*Primary Examiner* — Kimberly Chong
*Assistant Examiner* — Ruth Sophia Arieti
(74) *Attorney, Agent, or Firm* — Gowling WLG (Canada) LLP

(57) ABSTRACT

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject who is administered the one or more compositions. The target biomolecule is a precursor protein such as a precursor protein of CLTA4.

7 Claims, No Drawings

Specification includes a Sequence Listing.

SEQUENCE LISTING

```
Sequence total quantity: 3
SEQ ID NO: 1           moltype = DNA  length = 5840
FEATURE                Location/Qualifiers
source                 1..5840
                       mol_type = other DNA
                       organism = synthetic construct
SEQUENCE: 1
aatcaacctc tggattacaa aatttgtgaa agattgactg gtattcttaa ctatgttgct   60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aaccccact   240
ggttggggca ttgccaccac ctgtcagctc ctttccggga cttctcgcttt cccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
```

-continued

```
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccggcggcc tcagtgagcg agcgagcgcg ccagctggcg taatagcgaa  960
gaggcccgca ccgatcgccc ttcccaacag ttgcgcagcc tgaatggcga atggaattcc 1020
agacgattga gcgtcaaaat gtaggtattt ccatgagcgt ttttcctgtt gcaatggctg 1080
gcggtaatat tgttctggat attaccagca aggccgatag tttgagttct tctactcagg 1140
caagtgatgt tattactaat caaagaagta ttgcgacaac ggttaatttg cgtgatggac 1200
agactctttt actcggtggc ctcactgatt ataaaaacac ttctcaggat tctggcgtac 1260
cgttcctgtc taaaatccct ttaatcggcc tcctgtttag ctcccgctct gattctaacg 1320
aggaaagcac gttatacgtg ctcgtcaaag caaccatagt acgcgccctg tagcggcgca 1380
ttaagcgcgg cgggtgtggt ggttacgcgc agcgtgaccg ctacacttgc cagcgcccta 1440
gcgcccgctc ctttcgcttt cttcccttcc tttctcgcca cgttcgccgg ctttccccgt 1500
caagctctaa atcgggggct cccttttaggg ttccgattta gtgctttacg gcacctcgac 1560
cccaaaaaac ttgattaggg tgatggttca cgtagtgggc catcgcccctg atagacgggt 1620
tttcgccctt tgacgttgga gtccacgttc tttaatagtg gactcttgtt ccaaactgga 1680
acaacactca accctatctc ggtctattct tttgatttat aagggatttt gccgatttcg 1740
gcctattggt taaaaatga gctgatttaa caaaaattta acgcgaattt taacaaaata 1800
ttaacgttta caatttaaat atttgcttat acaatcttcc tgtttttggg gcttttctga 1860
ttatcaaccg gggtacatat gattgacatg ctagttttac gattaccgtt catcgattct 1920
cttgtttgct ccagactctc aggcaatgac ctgatagcct ttgtagagac ctctcaaaaa 1980
tagctaccct ctccggcatg aatttatcag ctagaacggt tgaatatcat attgatggtg 2040
atttgactgt ctccggcctt tctcacccgt ttgaatcttt acctacacat tactcaggca 2100
ttgcatttaa aatatatgag ggttctaaaa attttatcc ttgcgttgaa ataaaggctt 2160
ctcccgcaaa agtattacag ggtcataatg tttttggtac aaccgattta gctttatgct 2220
ctgaggcttt attgcttaat tttgctaatt cttttgcttg cctgtatgat ttattggatg 2280
ttggaattcc tgatgcggta ttttctcctt acgcatctgt gcggtatttc acaccgcata 2340
tggtgcactc tcagtacaat ctgctctgat gccgcatagt taagccagcc ccgacacccg 2400
ccaacacccg ctgacgcgcc ctgacgggct tgtctgctcc cggcatccgc ttacagacaa 2460
gctgtgaccg tctccgggag ctgcatgtgt cagaggtttt caccgtcatc accgaaacgc 2520
gcgagacgaa agggcctcgt gatacgccta ttttataggt taatgtcat gataataatg 2580
gtttcttaga cgtcaggtgg cacttttcgg ggaaatgtgc gcggaacccc tatttgttta 2640
tttttctaaa tacattcaaa tatgtatccg ctcatgagac aataaccctg ataaatgctt 2700
caataatatt gaaaaggaa gagtatgagt attcaacatt tccgtgtcgc ccttattccc 2760
tttttttgcgg cattttgcct tcctgttttt gctcacccag aaacgctggt gaaagtaaaa 2820
gatgctgaag atcagttggg tgcacgagtg ggttacatcg aactggatct caacagcggt 2880
aagatccttg agagttttcg ccccgaagaa cgttttccaa tgatgagcac ttttaaagtt 2940
ctgctatgtg gcgcggtatt atcccgtatt gacgccgggc aagagcaact cggtcgccgc 3000
atacactatt ctcagaatga cttggttgag tactcaccag tcacagaaaa gcatcttacg 3060
gatggcatga cagtaagaga attatgcagt gctgccataa ccatgagtga taacactgcg 3120
gccaacttac ttctgacaac gatcggagga ccgaaggagc taaccgcttt tttgcacaac 3180
atgggggatc atgtaactcg ccttgatcgt tgggaaccgg agctgaatga agccatacca 3240
aacgacgagc gtgacaccac gatgcctgta gcaatggcaa caacgttgcg caaactatta 3300
actggcgaac tacttactct agcttcccgg caacaattaa tagactggat ggaggcggat 3360
aaagttgcag gaccacttct gcgctcggcc cttccggctg gctggtttat tgctgataaa 3420
tctggagccg gtgagcgtgg gtctcgcggt atcattgcag cactggggcc agatggtaag 3480
ccctcccgta tcgtagttat ctacacgacg gggagtcagg caactatgga tgaacgaaat 3540
agacagatcg ctgagatagg tgcctcactg attaagcatt ggtaactgtc agaccaagtt 3600
tactcatata ctttagat tgatttaaaa cttcattttt aatttaaaag gatctaggtg 3660
aagatccttt ttgataatct catgaccaaa atcccttaac gtgagttttc gttccactga 3720
gcgtcagacc ccgtagaaaa gatcaaagga tcttcttgag atcctttttt tctgcgcgta 3780
atctgctgct tgcaaacaaa aaaaccaccg ctaccagcgg tggtttgttt gccggatcaa 3840
gagctaccaa ctcttttttcc gaaggtaact ggcttcagca gagcgcagat accaaatact 3900
gtccttctag tgtagccgta gttaggccac cacttcaaga actctgtagc accgcctaca 3960
tacctcgctc tgctaatcct gttaccagtg gctgctgcca gtggcgataa gtcgtgtctt 4020
accgggttgg actcaagacg atagttaccg gataaggcgc agcggtcggg ctgaacgggg 4080
ggttcgtgca cacagcccag cttggagcga acgacctaca ccgaactgag atacctacag 4140
cgtgagctat gagaaagcgc cacgcttccc gaaggtagaa aggcggacag gtatccggta 4200
agcggcaggg tcggaacagg agagcgcacg agggagcttc caggggggaaa cgcctggtat 4260
ctttatagtc ctgtcgggtt tcgccacctc tgacttgagc gtcgattttt gtgatgctcg 4320
tcaggggggc ggagcctatg gaaaaacgcc agcaacgcgg ccttttttacg gttcctggcc 4380
ttttgctggc cttttgctca catgttcttt cctgcgttat cccctgattc tgtggataac 4440
cgtattaccg cctttgagtg agctgatacc gctcgccgca gccgaacgac cgagcgcagc 4500
gagtcagtga gcgaggaagc ggaagagcgc ccaatacgca aaccgcctct ccccgcgcgt 4560
tggccgattc attaatgcag cagctgcgcg ctcgctcgct cactgaggcc gcccgggcaa 4620
agcccgggcg tcgggcgacc tttggtcgcc cggcctcagt gagcgagcga gcgcgcagag 4680
agggagtggc caactccatc actaggggtt ccttgtagtt aatgattaac cgccatgct 4740
acttatctac gtagccatgc tctaggacat tgattattga ctagtggagt tccgcgttac 4800
ataacttacg gtaaatggcc cgcctggctg accgcccaac gacccccgcc cattgacgtc 4860
aataatgacg tatgttccca tagtaacgcc aatagggact ttccattgac gtcaatgggt 4920
ggagtattta cggtaaactg cccacttggc agtacatcaa tgtatcata tgccaagtac 4980
gccccctatt gacgtcaatg acggtaaatg gcccgcctgg cattatgccc agtacatgac 5040
cttatgggac tttcctactt ggcagtacat ctacgtatta gtcatcgcta ttaccatggt 5100
cgaggtgagc cccacgttct gcttcactct ccccatctcc cccccctccc cacccccaat 5160
tttgtattta ttatttttt aattatttg tgcagcgatg ggggcgggg gggggggg 5220
cgcgcgccag gcggggcggg gcggggcgag gggcggggcg gggcgaggcg gagaggtgcg 5280
```

```
gcggcagcca atcagagcgg cgcgctccga aagtttcctt ttatggcgag gcggcggcgg      5340
cggcggccct ataaaagcg aagcgcgcgg cgggcgggag tcgctgcgcg ctgccttcgc       5400
cccgtgcccc gctccgccgc cgcctcgcgc cgcccgcccc ggctctgact gaccgcgtta      5460
ctaaaacagg taagtccggc ctccgcgccg gttttggcg cctcccgcgg cgcccccct       5520
cctcacggcg agcgctgcca cgtcagacga agggcgcagc gagcgtcctg atccttccgc      5580
ccggacgctc aggacagcgg cccgctgctc ataagactcg gccttagaac cccagtatca      5640
gcagaaggac attttaggac gggacttggg tgactctagg cactggttt tctttccaga      5700
gagcggaaca ggcgaggaaa agtagtccct tctcggcgat tctgcggagg gatctccgtg     5760
gggcggtgaa cgccgatgat gcctctacta accatgttca tgttttcttt ttttttctac     5820
aggtcctggg tgacgaacag                                                  5840

SEQ ID NO: 2            moltype = DNA   length = 756
FEATURE                 Location/Qualifiers
source                  1..756
                        mol_type = other DNA
                        organism = synthetic construct
SEQUENCE: 2
ggtaccgcca ccatgagggg catgaagctg ctggggcgc tgctggcact ggcggcccta       60
ctgcaggggg ccgtgtccat ggcgtgcctg ggctttcagc gccataaagc gcagctgaac     120
ctggcgaccc gcacctggcc gtgcaccctg ctgttttttc tgctgtttat tccggtgttt     180
tgcaaagcga tgcatgtggc gcagccggcg gtggtgctgg cgagcagccg cggcattgcg     240
agctttgtgt gcgaatatgc gagcccgggc aaagcgaccg aagtgcgcgt gaccgtgctg     300
cgccaggcgg atagccaggt gaccgaagtg tgcgcggcga cctatatgat gggcaacgaa     360
ctgacccttt tggatgatag catttgcacc ggcaccagca gcggcaacca ggtgaacctg     420
accattcagg gcctgcgcgc gatggatacc ggcctgtata tttgcaaagt ggaactgatg     480
tatccgccgc cgtattatct gggcattggc aacggcaccc agatttatgt gattgatccg     540
gaaccgtgcc cggatagcga ttttctgctg tggattctgg cggcggtgag cagcggcctg     600
tttttttata gctttctgct gaccgcggtg agcctgagca aaatgctgaa aaaacgcagc     660
ccgctgacca ccggcgtgta tgtgaaaatg ccgccgaccg aaccggaatg cgaaaaacag     720
tttcagccgt attttattcc gattaacttc tagaat                              756

SEQ ID NO: 3            moltype = DNA   length = 6596
FEATURE                 Location/Qualifiers
source                  1..6596
                        mol_type = other DNA
                        organism = synthetic construct
SEQUENCE: 3
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccccact    240
ggttgggca ttgccaccac ctgtcagctc ctttccggga ctttcgcttt ccccctccct     300
attgccacgg cggaactcat cgccgcctgc cttgcccgct gctggacagg ggctcggctg     360
ttgggcactg acaattccgt ggtgttgtcg gggaaatcat cgtcctttcc ttggctgctc     420
gcctgtgttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgc taagcttatc     600
gataccgtcg agatctaact tgtttattgc agcttataat ggttacaaat aaagcaatag     660
catcacaaat ttcacaaata aagcattttt ttcactgcat tctagttgtg gtttgtccaa     720
actcatcaat gtatcttatc atgtctggat ctcgacctcg actagagcat ggctacgtag     780
ataagtagca tggcgggtta atcattaact acaaggaacc cctagtgatg gagttggcca    840
ctccctctct gcgcgctcgc tcgctcactg aggccgggcg accaaaggtc gcccgacgcc     900
cgggctttgc ccgggcggcc tcagtgagcg agcgagcgcg ccagctgcg taatagcgaa     960
gaggcccgca ccgatcgccc ttcccaacag ttgcgcagcc tgaatggcga atggaattcc    1020
agacgattga gcgtcaaaat gtaggtattt tcatgagct ttttcctgtt gcaatggctg    1080
gcggtaatat tgttctggat attaccagca aggccgatag tttgagttct ctactcagg   1140
caagtgatgt tattactaat caaagaagta ttgcgacaac ggttaatttg cgtgatggac    1200
agactctttt actcggtggc ctcactgatt ataaaaacac ttctcaggat tctggcgtac    1260
cgttcctgtc taaaatccct ttaatcggcc tcctgtttag ctcccgctct gattctaacg    1320
aggaaagcac gttatacgtg tctcgtcaaa gcaaccatagt acgcgccctg tagcggcgca    1380
ttaagcgcgg cgggtgtggt ggttacgcgc agcgtgaccg ctacacttgc cagcgcccta    1440
gcgcccgctc ctttcgcttt cttccctccc tttctcgcca cgttcgccgg ctttccccgt    1500
caagctctaa atcgggggct ccctttaggg ttccgattta gtgctttacg gcacctcgac    1560
cccaaaaaac ttgattaggg tgatggttca cgtagtgggc catcgcccctg atagacggtt   1620
tttcgccctt tgacgttgga gtccacgttc tttaatagtg gactcttgtt ccaaactgga    1680
acaacactca accctatctc ggtctattct tttgatttat aagggatttt gccgatttcg    1740
gcctattggt taaaaaatga gctgatttaa caaaaattta cgcgaattt taacaaaata    1800
ttaacgttta caatttaaat atttgcttat acaatcttcc tgttttttggg gcttttctga    1860
ttatcaaccg gggtacatat gattgacatg ctagttttac gattaccgtt catcgattct    1920
cttgtttgct ccagactctc aggcaatgac ctgatagcct tgtagagac ctctcaaaaa     1980
tagctacccct ctccggcatg aatttatcag ctagaacgt tgaatatcat attgatggtg    2040
atttgactgt ctccggcctt tctcacccgt ttgaatcttt acctacacat tactcaggca    2100
ttgcatttaa aatatgagg ggttctaaaa attttatcc ttgcgttgaa ataaggctt     2160
ctcccgcaaa agtattacag gcatataagt attttggtac aacgatttta gcttatgct    2220
ctgaggcttt attgcttaat tttgctaatt ctttgccttg cctgtatgat ttattggatg    2280
ttggaattcc tgatgcggta ttttctcctt acgcatctgt gcggtatttc acaccgcata    2340
tggtgcactc tcagtacaat ctgctctgat gccgcatagt taagcagcc ccgacacccg    2400
ccaaccccg ctgacgcgcc ctgacgggct tgtctgctcc cggcatccgc ttacagacaa    2460
gctgtgaccg tctccgggag ctgcatgtgt cagaggtttt caccgtcatc accgaaacgc    2520
```

```
gcgagacgaa agggcctcgt gatacgccta ttttatagg ttaatgtcat gataataatg   2580
gtttcttaga cgtcaggtgg cacttttcgg ggaaatgtgc gcggaacccc tatttgttta   2640
tttttctaaa tacattcaaa tatgtatccg ctcatgagac aataaccctg ataaatgctt   2700
caataatatt gaaaaggaa gagtatgagt attcaacatt tccgtgtcgc ccttattccc   2760
tttttttgcgg catttttgcct tcctgttttt gctcacccag aaacgctggt gaaagtaaaa   2820
gatgctgaag atcagttggg tgcacgagtg gttacatcg aactggatct caacagcggt   2880
aagatccttg agagttttcg ccccgaagaa cgttttccaa tgatgagcac ttttaaagtt   2940
ctgctatgtg gcgcggtatt atcccgtatt gacgccgggc aagagcaact cggtcgccgc   3000
atacactatt ctcagaatga cttggttgag tactcaccag tcacagaaaa gcatcttacg   3060
gatggcatga cagtaagaga attatgcagt gctgccataa ccatgagtga taacactgcg   3120
gccaacttac ttctgacaac gatcggagga ccgaaggagc taaccgcttt tttgcacaac   3180
atgggggatc atgtaactcg ccttgatcgt tgggaaccgg agctgaatga agccatacca   3240
aacgacgagc gtgacaccac gatgcctgta gcaatggcaa caacgttgcg caaactatta   3300
actggcgaac tacttactct agcttccgg caacaattaa tagactggat ggaggcggat   3360
aaagttgcag gaccacttct gcgctcggcc cttccggctg gctggtttat tgctgataaa   3420
tctggagccg gtgagcgtgg gtctcgcggt atcattgcag cactggggcc agatggtaag   3480
ccctcccgta tcgtagttat ctacacgacg gggagtcagg caactatgga tgaacgaaat   3540
agacagatcg ctgagatagg tgcctcactg attaagcatt ggtaactgtc agaccaagtt   3600
tactcatata ctttagat tgatttaaaa cttcattttt aatttaaaag gatctaggtg   3660
aagatccttt ttgataatct catgaccaaa atcccttaac gtgagttttc gttccactga   3720
gcgtcagacc ccgtagaaaa gatcaaagga tcttcttgag atccttttt tctgcgcgta   3780
atctgctgct tgcaaacaaa aaaaccaccg ctaccagcgg tggtttgttt gccggatcaa   3840
gagctaccaa ctctttttcc gaaggtaact ggcttcagca gagcgcagat accaaatact   3900
gtccttctag tgtagccgta gttaggccac cacttcaaga actctgtagc accgcctaca   3960
tacctcgctc tgctaatcct gttaccagtg gctgctgcca gtggcgataa gtcgtgtctt   4020
accgggttgg actcaagacg atagttaccg gataaggcgc agcggtcggg ctgaacgggg   4080
ggttcgtgca cacagcccag cttggagcga acgacctaca ccgaactgag atacctacag   4140
cgtgagctat gagaaagcgc cacgcttccc gaagggagaa aggcggacag gtatccggta   4200
agcggcaggg tcggaacagg agagcgcacg agggagcttc caggggggaaa cgcctggtat   4260
ctttatagtc ctgtcgggtt tcgccacctc tgacttgagc gtcgatttt gtgatgctcg   4320
tcagggggggc ggagcctatg gaaaaacgcc agcaacgcgg cctttttacg gttcctggcc   4380
ttttgctggc cttttgctca catgttcttt cctgcgttat cccctgattc tgtggataac   4440
cgtattaccg cctttgagtg agctgatacc gctcgccgca gccgaacgac cgagcgcagc   4500
gagtcagtga gcgaggaagc ggaagagcgc ccaatacgca aaccgcctct ccccgcgcgt   4560
tggccgattc attaatgcag cagctgcgcg ctcgctcgct cactgaggcc gcccgggcaa   4620
agcccgggcg tcgggcgacc tttggtcgcc cggcctcagt gagcgagcga gcgcgcagag   4680
agggagtggc caactccatc actaggggtt ccttgtagtt aatgattaac ccgccatgct   4740
acttatctac gtagccatgc tctaggacat tgattattga ctagtggagt tccgcgttac   4800
ataacttacg gtaaatggcc cgcctggctg accgcccaac gacccccgcc cattgacgtc   4860
aataatgacg tatgttccca tagtaacgcc aataggggact ttccattgac gtcaatgggt   4920
ggagtattta cggtaaactg cccacttggc agtacatcaa gtgtatcata tgccaagtac   4980
gccccctatt gacgtcaatg acggtaaatg gcccgcctgg cattatgccc agtacatgac   5040
cttatgggac tttcctactt ggcagtacat ctacgtatta gtcatcgcta ttaccatggt   5100
cgaggtgagc cccacgttct gcttcactct ccccatctcc ccccctccc caccccaat   5160
tttgtattta tttatttttt aattattttg tgcagcgatg ggggcggggg ggggggggg   5220
cgcgcgccag gcggggcggg gcggggcgag gggcggggcg gggcgaggcg gagaggtgcg   5280
gcggcagcca atcagagcgg cgcgctccga aagtttcctt ttatggcgag gcggcggcgg   5340
cggcggccct ataaaaagcg aagcgcgcgg cgggcgggag tcgctgcgcg ctgccttcgc   5400
cccgtgcccc gctccgccgc cgcctcgcgc cgcccgcccc ggctctgact gaccgcgtta   5460
ctaaaacagg taagtccggc ctccgcgccg ggttttggcg cctcccgcgg gcgcccccct   5520
cctcacggcg agcgctgcca cgtcagacga agggcgcagc gagcgtcctg atccttccgc   5580
ccggacgctc aggacagcgg cccgctgctc ataagactcg gccttagaac cccagtatca   5640
gcagaaggac attttaggac gggacttggg tgactctagg gcactggttt tcttttccaga   5700
gagcggaaca ggcgaggaaa agtagtccct tctcggagat tctgcggagg gatctccgtg   5760
gggcggtgaa cgccgatgat gcctctacta accatgttca tgttttcttt ttttttctac   5820
aggtcctggg tgacgaacag ggtaccgcca ccatgagggg catgaagctg ctggggcgc   5880
tgctggcact ggcggcccta ctgcagggg ccgtgtccat ggcgtgcctg gctttcagc   5940
gccataaagc gcagctgaac ctggcgaccc gcacctggcc gtgcaccctg ctgtttttc   6000
tgctgtttat tccggtgttt tgcaaagcga tgcatgtggc gcagccggcg gtggtgctgg   6060
cgagcagccg cggcattgcg agctttgtgt gcgaatatgc gagcccgggc aaagcgaccg   6120
aagtgcgcgt gaccgtgctg cgccaggcgg atagccaggt gaccgaagtg tgcgcggcga   6180
cctatatgat gggcaacgaa ctgacccttc tggatgatag catttgcacc ggcaccagca   6240
gcggcaacca ggtgaacctg accattcagg gcctgcgcgc gatggatacc ggcctgtata   6300
tttgcaaagt ggaactgatg tatccgccgc cgtattatct gggcattggt aacggcaccc   6360
agatttatgt gattgatccg gaaccgtgcc cggatagcga ttttctgctg tggattctgg   6420
cggcggtgag cagcggcctg ttttttata gctttctgct gaccgcgtg agcctgagca   6480
aaatgctgaa aaaacgcagc ccgctgacca ccggcgtgta tgtgaaaatg ccgccgaccg   6540
aaccggaatg cgaaaaacag tttcagccgt attttattcc gattaacttc tagaat       6596
```

COMPOSITION FOR REGULATING PRODUCTION OF PROTEINS

This application contains a Sequence Listing electronically submitted via Patent Center to the United States Patent and Trademark Office as an XML Document file entitled "A8149547US-Sequence Listing ST26.xml" created on Jun. 4, 2024 and having a size of 16,416 bytes. The information contained in the Sequence Listing is incorporated by reference herein.

TECHNICAL FIELD

The present disclosure generally relates to compositions for regulating the production of precursor proteins. In particular, the present disclosure relates to compositions for regulating gene expression that results in the production of precursor proteins.

BACKGROUND

Bioactive molecules, including checkpoint molecules, are necessary for the homeostatic control of biological systems. When bioactive molecules are under-expressed or mis-expressed, homeostasis is lost, and disease is often the result.

As such, it may be desirable to establish therapies, treatments and/or interventions that address the loss of homeostasis and the regulation of bioactive molecules in order to prevent or treat the resulting disease.

SUMMARY

Some embodiments of the present disclosure relate to one or more compositions that upregulate the production of one or more sequences of messenger ribonucleic acid (mRNA). The sequences of mRNA may encode for translation of a target biomolecule, thereby causing an increase in bioavailability of the target biomolecule within a subject that is administered the one or more compositions. In some embodiments of the present disclosure, the target biomolecule is a precursor protein such as the precursor protein of cytotoxic T-lymphocyte associated protein 4 (CTLA4).

In some embodiments of the present disclosure the compositions comprise a plasmid of deoxyribonucleic acid (DNA) that includes one or more insert sequences of nucleic acids that encode for the production of mRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of mRNA and, consequently, increased translation of the target biomolecule by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding an mRNA sequence that encodes for a precursor protein of CTLA4.

Some embodiments of the present disclosure relate to a method of making a composition/target cell complex. The method comprising a step of administering a RP comprising SEQ ID NO. 1 and SEQ ID NO. 2 to a target cell for forming the composition/target cell complex, wherein the composition/target cell complex causes the target cell to increase production of one or more sequences of mRNA that increase production of a target biomolecule.

Embodiments of the present disclosure relate to at least one approach for inducing endogenous production of one or more sequences of mRNA that encode for a target biomolecule, for example a precursor protein of CTLA4. A first approach utilizes gene vectors containing nucleotide sequences for increasing the endogenous production of one or more sequences of mRNA, which are complete or partial sequences and/or combinations thereof of a precursor protein of CTLA4, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the terms "production", "producing" and "produce" refer to the synthesis and/or replication of DNA, the transcription of one or more sequences of RNA, the translation of one or more amino acid sequences, the post-translational modifications of an amino acid sequence, and/ or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a precursor protein molecule that is found within a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of mRNA that increases the production of target biomolecules, such as a precursor protein.

In some embodiments of the present disclosure, the target biomolecule is a precursor protein of cytotoxic T-lymphocyte associated protein 4 (CTLA4). As will be appreciated by those skilled in the art, a precursor protein is an amino-acid based ribosomal product of the translation process that has no or different biological activity than the final protein product of post-translational modification. As such, the embodiments of the present disclosure result in an increased bioavailability of a target biomolecule that is a sequence of amino acids that have not yet undergone post-translational modification. The embodiments of the present disclosure relate to a precursor protein of CTLA-4, which is also known as CD 152. This precursor protein does not act as a receptor protein that can downregulate an immune-response when ligand bound, as the CTLA-4 protein does. Without being bound by any particular theory, an increased bioavailability of the CTLA-4 precursor allows a subject to have a more readily accessible reserve of CTLA-4 precursor proteins that can then undergo post-translational modification in order to increase the bioavailability of CTLA-4 proteins, perhaps in a shorter process to provide such a readily accessible reserve of CTLA-4 precursor proteins that would otherwise require transcription of the CTLA-4 gene to occur in order to generate a CTLA-4 precursor protein.

Some embodiments of the present disclosure relate to a composition that can be administered to a subject with a condition that results, directly or indirectly, from the dysregulated production of a biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both of one or more sequences of mRNA that each encode for one or more biomolecules.

In some embodiments of the present disclosure, the composition is an RP that may be used for gene therapy. The gene therapy is useful for increasing the subject's endogenous production of one or more sequences of mRNA that encode for a target biomolecule. For example, the RP can contain one or more nucleotide sequences that cause increased production of one or more nucleotide sequences that cause an increased production of one or more mRNA sequences that encode for one biomolecule, such as a precursor protein of CTLA-4.

In some embodiments of the present disclosure, the delivery vehicle of the RP used for gene therapy may be a vector that comprises a virus that can be enveloped or not (un-enveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus *Dependoparvovirus*. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ TCID$_{50}$/kg (50% tissue culture infective dose per kilogram of the patient's body mass). In some embodiments of the present disclosure, the therapeutically effective amount of the composition that is administered to the patient is about $1 \times 10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1 \times 10^{16}$ TCP/kg.

Some embodiments of the present disclosure relate to an adeno-associated virus (AAV) genome consisting of a RP that when operable inside a target cell will cause the target cell to produce a mRNA sequence that upregulates production of a biomolecule, with examples being a precursor protein of CTLA4. The RP is comprised of AAV2 inverted terminal repeats (ITRs), a composite CASI promoter, and a human growth hormone (HGH) signal peptide followed by a mRNA expression cassette encoding for the precursor protein of CTLA4, followed by a Woodchuck Hepatitis Virus post-transcriptional regulatory element (WPRE) and a Simian virus 40 (SV40) polyadenylation (polyA) signal.

SEQ ID NO. 1 (backbone sequence No. 1):
5'

AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAG

GAGTTGTGGCCCGTTGTCAGGCAACGTGGCGTGGTGTGCACTGTGTTTGCTGACGCA

ACCCCCACTGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAATCATCGT

CCTTTCCTTGGCTGCTCGCCTGTGTTGCCACCTGGATTCTGCGCGGGACGTCCTTCTG

CTACGTCCCTTCGGCCCTCAATCCAGCGGACCTTCCTTCCCGCGGCCTGCTGCCGGCT

CTGCGGCCTCTTCCGCGTCTTCGCCTTCGCCCTCAGACGAGTCGGATCTCCCTTTGGG

CCGCCTCCCCGCCTAAGCTTATCGATACCGTCGAGATCTAACTTGTTTATTGCAGCTT

ATAATGGTTACAAATAAAGCAATAGCATCACAAATTTCACAAATAAAGCATTTTTTT

CACTGCATTCTAGTTGTGGTTTGTCCAAACTCATCAATGTATCTTATCATGTCTGGAT

CTCGACCTCGACTAGAGCATGGCTACGTAGATAAGTAGCATGGCGGGTTAATCATTA

ACTACAAGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGGCGGCC

TCAGTGAGCGAGCGAGCGCGCCAGCTGGCGTAATAGCGAAGAGGCCCGCACCGATC

GCCCTTCCCAACAGTTGCGCAGCCTGAATGGCGAATGGAATTCCAGACGATTGAGC

GTCAAAATGTAGGTATTTCCATGAGCGTTTTTCCTGTTGCAATGGCTGGCGGTAATA

TTGTTCTGGATATTACCAGCAAGGCCGATAGTTTGAGTTCTTCTACTCAGGCAAGTG

ATGTTATTACTAATCAAAGAAGTATTGCGACAACGGTTAATTTGCGTGATGGACAGA

CTCTTTTACTCGGTGGCCTCACTGATTATAAAAACACTTCTCAGGATTCTGGCGTACC

GTTCCTGTCTAAAATCCCTTTAATCGGCCTCCTGTTTAGCTCCCGCTCTGATTCTAAC

-continued

```
GAGGAAAGCACGTTATACGTGCTCGTCAAAGCAACCATAGTACGCGCCCTGTAGCG

GCGCATTAAGCGCGGCGGGTGTGGTGGTTACGCGCAGCGTGACCGCTACACTTGCC

AGCGCCCTAGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTTAGTGCTTT

ACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGA

CTCTTGTTCCAAACTGGAACAACACTCAACCCTATCTCGGTCTATTCTTTTGATTTAT

AAGGGATTTTGCCGATTTCGGCCTATTGGTTAAAAAATGAGCTGATTTAACAAAAAT

TTAACGCGAATTTTAACAAAATATTAACGTTTACAATTTAAATATTTGCTTATACAAT

CTTCCTGTTTTTGGGGCTTTTCTGATTATCAACCGGGGTACATATGATTGACATGCTA

GTTTTACGATTACCGTTCATCGATTCTCTTGTTTGCTCCAGACTCTCAGGCAATGACC

TGATAGCCTTTGTAGAGACCTCTCAAAAATAGCTACCCTCTCCGGCATGAATTTATC

AGCTAGAACGGTTGAATATCATATTGATGGTGATTTGACTGTCTCCGGCCTTTCTCAC

CCGTTTGAATCTTTACCTACACATTACTCAGGCATTGCATTTAAAATATATGAGGGTT

CTAAAAATTTTTATCCTTGCGTTGAAATAAAGGCTTCTCCCGCAAAAGTATTACAGG

GTCATAATGTTTTGGTACAACCGATTTAGCTTTATGCTCTGAGGCTTTATTGCTTAA

TTTTGCTAATTCTTTGCCTTGCCTGTATGATTTATTGGATGTTGGAATTCCTGATGCG

GTATTTTCTCCTTACGCATCTGTGCGGTATTTCACACCGCATATGGTGCACTCTCAGT

ACAATCTGCTCTGATGCCGCATAGTTAAGCCAGCCCCGACACCCGCCAACACCCGCT

GACGCGCCCTGACGGGCTTGTCTGCTCCCGGCATCCGCTTACAGACAAGCTGTGACC

GTCTCCGGGAGCTGCATGTGTCAGAGGTTTTCACCGTCATCACCGAAACGCGCGAGA

CGAAAGGGCCTCGTGATACGCCTATTTTTATAGGTTAATGTCATGATAATAATGGTT

TCTTAGACGTCAGGTGGCACTTTTCGGGGAAATGTGCGCGGAACCCCTATTTGTTTA

TTTTTCTAAATACATTCAAATATGTATCCGCTCATGAGACAATAACCCTGATAAATG

CTTCAATAATATTGAAAAAGGAAGAGTATGAGTATTCAACATTTCCGTGTCGCCCTT

ATTCCCTTTTTTGCGGCATTTTGCCTTCCTGTTTTTGCTCACCCAGAAACGCTGGTGA

AAGTAAAAGATGCTGAAGATCAGTTGGGTGCACGAGTGGGTTACATCGAACTGGAT

CTCAACAGCGGTAAGATCCTTGAGAGTTTTCGCCCCGAAGAACGTTTTCCAATGATG

AGCACTTTTAAAGTTCTGCTATGTGGCGCGGTATTATCCCGTATTGACGCCGGGCAA

GAGCAACTCGGTCGCCGCATACACTATTCTCAGAATGACTTGGTTGAGTACTCACCA

GTCACAGAAAAGCATCTTACGGATGGCATGACAGTAAGAGAATTATGCAGTGCTGC

CATAACCATGAGTGATAACACTGCGGCCAACTTACTTCTGACAACGATCGGAGGAC

CGAAGGAGCTAACCGCTTTTTTGCACAACATGGGGGATCATGTAACTCGCCTTGATC

GTTGGGAACCGGAGCTGAATGAAGCCATACCAAACGACGAGCGTGACACCACGATG

CCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACT

TCTGCGCTCGGCCCTTCCGGCTGGCTGGTTTATTGCTGATAAATCTGGAGCCGGTGA

GCGTGGGTCTCGCGGTATCATTGCAGCACTGGGGCCAGATGGTAAGCCCTCCCGTAT

CGTAGTTATCTACACGACGGGGAGTCAGGCAACTATGGATGAACGAAATAGACAGA

TCGCTGAGATAGGTGCCTCACTGATTAAGCATTGGTAACTGTCAGACCAAGTTTACT
```

-continued

```
CATATATACTTTAGATTGATTTAAAACTTCATTTTTAATTTAAAAGGATCTAGGTGAA
GATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTA
GCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCA
GCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGAGCGCA
CGAGGGAGCTTCCAGGGGGAAACGCCTGGTATCTTTATAGTCCTGTCGGGTTTCGCC
ACCTCTGACTTGAGCGTCGATTTTTGTGATGCTCGTCAGGGGGGCGGAGCCTATGGA
AAAACGCCAGCAACGCGGCCTTTTTACGGTTCCTGGCCTTTTGCTGGCCTTTTGCTCA
CATGTTCTTTCCTGCGTTATCCCCTGATTCTGTGGATAACCGTATTACCGCCTTTGAG
TGAGCTGATACCGCTCGCCGCAGCCGAACGACCGAGCGCAGCGAGTCAGTGAGCGA
GGAAGCGGAAGAGCGCCCAATACGCAAACCGCCTCTCCCCGCGCGTTGGCCGATTC
ATTAATGCAGCAGCTGCGCGCTCGCTCGCTCACTGAGGCCGCCCGGGCAAAGCCCG
GGCGTCGGGCGACCTTTGGTCGCCCGGCCTCAGTGAGCGAGCGAGCGCGCAGAGAG
GGAGTGGCCAACTCCATCACTAGGGGTTCCTTGTAGTTAATGATTAACCCGCCATGC
TACTTATCTACGTAGCCATGCTCTAGGACATTGATTATTGACTAGTGGAGTTCCGCGT
TACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACG
TCAATGGGTGGAGTATTTACGGTAAACTGCCCACTTGGCAGTACATCAAGTGTATCA
TATGCCAAGTACGCCCCCTATTGACGTCAATGACGGTAAATGGCCCGCCTGGCATTA
TGCCCAGTACATGACCTTATGGGACTTTCCTACTTGGCAGTACATCTACGTATTAGTC
ATCGCTATTACCATGGTCGAGGTGAGCCCCACGTTCTGCTTCACTCTCCCCATCTCCC
CCCCCTCCCCACCCCCAATTTTGTATTTATTTATTTTTTAATTATTTTGTGCAGCGATG
GGGGGGGGGGGGGGGGGGCGCGCGCCAGGCGGGGCGGGGCGGGGCGAGGGGC
GGGGCGGGGCGAGGCGGAGAGGTGCGGCGGCAGCCAATCAGAGCGGCGCGCTCCG
AAAGTTTCCTTTTATGGCGAGGCGGCGGCGGCGGCGGCCCTATAAAAAGCGAAGCG
CGCGGCGGGCGGGAGTCGCTGCGCGCTGCCTTCGCCCCGTGCCCCGCTCCGCCGCCG
CCTCGCGCCGCCCGCCCCGGCTCTGACTGACCGCGTTACTAAAACAGGTAAGTCCGG
CCTCCGCGCCGGGTTTTGGCGCCTCCCGCGGGCGCCCCCCTCCTCACGGCGAGCGCT
GCCACGTCAGACGAAGGGCGCAGCGAGCGTCCTGATCCTTCCGCCCGGACGCTCAG
GACAGCGGCCCGCTGCTCATAAGACTCGGCCTTAGAACCCCAGTATCAGCAGAAGG
ACATTTTAGGACGGGACTTGGGTGACTCTAGGGCACTGGTTTTCTTTCCAGAGAGCG
GAACAGGCGAGGAAAAGTAGTCCCTTCTCGGCGATTCTGCGGAGGGATCTCCGTGG
GGCGGTGAACGCCGATGATGCCTCTACTAACCATGTTCATGTTTTCTTTTTTTTCTA
CAGGTCCTGGGTGACGAACAG
```

3'

-continued

SEQ ID NO. 2 (mRNA expression cassette No. 2 - precursor CTLA4):
5'

GGTACCGCCACCATGAGGGGCATGAAGCTGCTGGGGGCGCTGCTGGCACTGGCGGC

CCTACTGCAGGGGGCCGTGTCCATGGCGTGCCTGGGCTTTCAGCGCCATAAAGCGCA

GCTGAACCTGGCGACCCGCACCTGGCCGTGCACCCTGCTGTTTTTTCTGCTGTTTATT

CCGGTGTTTTGCAAAGCGATGCATGTGGCGCAGCCGGCGGTGGTGCTGGCGAGCAG

CCGCGGCATTGCGAGCTTTGTGTGCGAATATGCGAGCCCGGGCAAAGCGACCGAAG

TGCGCGTGACCGTGCTGCGCCAGGCGGATAGCCAGGTGACCGAAGTGTGCGCGGCG

ACCTATATGATGGGCAACGAACTGACCTTTCTGGATGATAGCATTTGCACCGGCACC

AGCAGCGGCAACCAGGTGAACCTGACCATTCAGGGCCTGCGCGCGATGGATACCGG

CCTGTATATTTGCAAAGTGGAACTGATGTATCCGCCGCCGTATTATCTGGGCATTGG

CAACGGCACCCAGATTTATGTGATTGATCCGGAACCGTGCCCGGATAGCGATTTTCT

GCTGTGGATTCTGGCGGCGGTGAGCAGCGGCCTGTTTTTTTATAGCTTTCTGCTGACC

GCGGTGAGCCTGAGCAAAATGCTGAAAAAACGCAGCCCGCTGACCACCGGCGTGTA

TGTGAAAATGCCGCCGACCGAACCGGAATGCGAAAAACAGTTTCAGCCGTATTTTAT

TCCGATTAACTTCTAGAAT

3'

SEQ ID NO. 3 = SEQ ID NO. 1 + SEQ ID NO. 2
5'

AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAG

GAGTTGTGGCCCGTTGTCAGGCAACGTGGCGTGGTGTGCACTGTGTTTGCTGACGCA

ACCCCCACTGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAATCATCGT

CCTTTCCTTGGCTGCTCGCCTGTGTTGCCACCTGGATTCTGCGCGGGACGTCCTTCTG

CTACGTCCCTTCGGCCCTCAATCCAGCGGACCTTCCTTCCCGCGGCCTGCTGCCGGCT

CTGCGGCCTCTTCCGCGTCTTCGCCTTCGCCCTCAGACGAGTCGGATCTCCCTTTGGG

CCGCCTCCCCGCCTAAGCTTATCGATACCGTCGAGATCTAACTTGTTTATTGCAGCTT

ATAATGGTTACAAATAAAGCAATAGCATCACAAATTTCACAAATAAAGCATTTTTTT

CACTGCATTCTAGTTGTGGTTTGTCCAAACTCATCAATGTATCTTATCATGTCTGGAT

CTCGACCTCGACTAGAGCATGGCTACGTAGATAAGTAGCATGGCGGGTTAATCATTA

ACTACAAGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGGCGGCC

TCAGTGAGCGAGCGAGCGCGCCAGCTGGCGTAATAGCGAAGAGGCCCGCACCGATC

GCCCTTCCCAACAGTTGCGCAGCCTGAATGGCGAATGGAATTCCAGACGATTGAGC

GTCAAAATGTAGGTATTTCCATGAGCGTTTTTCCTGTTGCAATGGCTGGCGGTAATA

TTGTTCTGGATATTACCAGCAAGGCCGATAGTTTGAGTTCTTCTACTCAGGCAAGTG

ATGTTATTACTAATCAAAGAAGTATTGCGACAACGGTTAATTTGCGTGATGGACAGA

CTCTTTTACTCGGTGGCCTCACTGATTATAAAAACACTTCTCAGGATTCTGGCGTACC

-continued

```
GTTCCTGTCTAAAATCCCTTTAATCGGCCTCCTGTTTAGCTCCCGCTCTGATTCTAAC

GAGGAAAGCACGTTATACGTGCTCGTCAAAGCAACCATAGTACGCGCCCTGTAGCG

GCGCATTAAGCGCGGCGGGTGTGGTGGTTACGCGCAGCGTGACCGCTACACTTGCC

AGCGCCCTAGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTTAGTGCTTT

ACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGA

CTCTTGTTCCAAACTGGAACAACACTCAACCCTATCTCGGTCTATTCTTTTGATTTAT

AAGGGATTTTGCCGATTTCGGCCTATTGGTTAAAAAATGAGCTGATTTAACAAAAAT

TTAACGCGAATTTTAACAAAATATTAACGTTTACAATTTAAATATTTGCTTATACAAT

CTTCCTGTTTTTGGGGCTTTTCTGATTATCAACCGGGGTACATATGATTGACATGCTA

GTTTTACGATTACCGTTCATCGATTCTCTTGTTTGCTCCAGACTCTCAGGCAATGACC

TGATAGCCTTTGTAGAGACCTCTCAAAAATAGCTACCCTCTCCGGCATGAATTTATC

AGCTAGAACGGTTGAATATCATATTGATGGTGATTTGACTGTCTCCGGCCTTTCTCAC

CCGTTTGAATCTTTACCTACACATTACTCAGGCATTGCATTTAAAATATATGAGGGTT

CTAAAAATTTTTATCCTTGCGTTGAAATAAAGGCTTCTCCCGCAAAAGTATTACAGG

GTCATAATGTTTTGGTACAACCGATTTAGCTTTATGCTCTGAGGCTTTATTGCTTAA

TTTTGCTAATTCTTTGCCTTGCCTGTATGATTTATTGGATGTTGGAATTCCTGATGCG

GTATTTTCTCCTTACGCATCTGTGCGGTATTTCACACCGCATATGGTGCACTCTCAGT

ACAATCTGCTCTGATGCCGCATAGTTAAGCCAGCCCCGACACCCGCCAACACCCGCT

GACGCGCCCTGACGGGCTTGTCTGCTCCCGGCATCCGCTTACAGACAAGCTGTGACC

GTCTCCGGGAGCTGCATGTGTCAGAGGTTTTCACCGTCATCACCGAAACGCGCGAGA

CGAAAGGGCCTCGTGATACGCCTATTTTTATAGGTTAATGTCATGATAATAATGGTT

TCTTAGACGTCAGGTGGCACTTTTCGGGGAAATGTGCGCGGAACCCCTATTTGTTTA

TTTTTCTAAATACATTCAAATATGTATCCGCTCATGAGACAATAACCCTGATAAATG

CTTCAATAATATTGAAAAAGGAAGAGTATGAGTATTCAACATTTCCGTGTCGCCCTT

ATTCCCTTTTTTGCGGCATTTTGCCTTCCTGTTTTTGCTCACCCAGAAACGCTGGTGA

AAGTAAAAGATGCTGAAGATCAGTTGGGTGCACGAGTGGGTTACATCGAACTGGAT

CTCAACAGCGGTAAGATCCTTGAGAGTTTTCGCCCCGAAGAACGTTTTCCAATGATG

AGCACTTTTAAAGTTCTGCTATGTGGCGCGGTATTATCCCGTATTGACGCCGGGCAA

GAGCAACTCGGTCGCCGCATACACTATTCTCAGAATGACTTGGTTGAGTACTCACCA

GTCACAGAAAAGCATCTTACGGATGGCATGACAGTAAGAGAATTATGCAGTGCTGC

CATAACCATGAGTGATAACACTGCGGCCAACTTACTTCTGACAACGATCGGAGGAC

CGAAGGAGCTAACCGCTTTTTTGCACAACATGGGGGATCATGTAACTCGCCTTGATC

GTTGGGAACCGGAGCTGAATGAAGCCATACCAAACGACGAGCGTGACACCACGATG

CCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACT

TCTGCGCTCGGCCCTTCCGGCTGGCTGGTTTATTGCTGATAAATCTGGAGCCGGTGA

GCGTGGGTCTCGCGGTATCATTGCAGCACTGGGGCCAGATGGTAAGCCCTCCCGTAT

CGTAGTTATCTACACGACGGGGAGTCAGGCAACTATGGATGAACGAAATAGACAGA
```

-continued

```
TCGCTGAGATAGGTGCCTCACTGATTAAGCATTGGTAACTGTCAGACCAAGTTTACT

CATATATACTTTAGATTGATTTAAAACTTCATTTTTAATTTAAAAGGATCTAGGTGAA

GATCCTTTTTGATAATCTCATGACCAAAATCCCTTAACGTGAGTTTTCGTTCCACTGA

GCGTCAGACCCCGTAGAAAAGATCAAAGGATCTTCTTGAGATCCTTTTTTTCTGCGC

GTAATCTGCTGCTTGCAAACAAAAAAACCACCGCTACCAGCGGTGGTTTGTTTGCCG

GATCAAGAGCTACCAACTCTTTTTCCGAAGGTAACTGGCTTCAGCAGAGCGCAGATA

CCAAATACTGTCCTTCTAGTGTAGCCGTAGTTAGGCCACCACTTCAAGAACTCTGTA

GCACCGCCTACATACCTCGCTCTGCTAATCCTGTTACCAGTGGCTGCTGCCAGTGGC

GATAAGTCGTGTCTTACCGGGTTGGACTCAAGACGATAGTTACCGGATAAGGCGCA

GCGGTCGGGCTGAACGGGGGGTTCGTGCACACAGCCCAGCTTGGAGCGAACGACCT

ACACCGAACTGAGATACCTACAGCGTGAGCTATGAGAAAGCGCCACGCTTCCCGAA

GGGAGAAAGGCGGACAGGTATCCGGTAAGCGGCAGGGTCGGAACAGGAGAGCGCA

CGAGGGAGCTTCCAGGGGGAAACGCCTGGTATCTTTATAGTCCTGTCGGGTTTCGCC

ACCTCTGACTTGAGCGTCGATTTTTGTGATGCTCGTCAGGGGGGCGGAGCCTATGGA

AAAACGCCAGCAACGCGGCCTTTTTACGGTTCCTGGCCTTTTGCTGGCCTTTTGCTCA

CATGTTCTTTCCTGCGTTATCCCCTGATTCTGTGGATAACCGTATTACCGCCTTTGAG

TGAGCTGATACCGCTCGCCGCAGCCGAACGACCGAGCGCAGCGAGTCAGTGAGCGA

GGAAGCGGAAGAGCGCCCAATACGCAAACCGCCTCTCCCCGCGCGTTGGCCGATTC

ATTAATGCAGCAGCTGCGCGCTCGCTCGCTCACTGAGGCCGCCCGGGCAAAGCCCG

GGCGTCGGGCGACCTTTGGTCGCCCGGCCTCAGTGAGCGAGCGAGCGCGCAGAGAG

GGAGTGGCCAACTCCATCACTAGGGGTTCCTTGTAGTTAATGATTAACCCGCCATGC

TACTTATCTACGTAGCCATGCTCTAGGACATTGATTATTGACTAGTGGAGTTCCGCGT

TACATAACTTACGGTAAATGGCCCGCCTGGCTGACCGCCCAACGACCCCCGCCCATT

GACGTCAATAATGACGTATGTTCCCATAGTAACGCCAATAGGGACTTTCCATTGACG

TCAATGGGTGGAGTATTTACGGTAAACTGCCCACTTGGCAGTACATCAAGTGTATCA

TATGCCAAGTACGCCCCCTATTGACGTCAATGACGGTAAATGGCCCGCCTGGCATTA

TGCCCAGTACATGACCTTATGGGACTTTCCTACTTGGCAGTACATCTACGTATTAGTC

ATCGCTATTACCATGGTCGAGGTGAGCCCCACGTTCTGCTTCACTCTCCCCATCTCCC

CCCCCTCCCCACCCCCAATTTTGTATTTATTTATTTTTTAATTATTTTGTGCAGCGATG

GGGGGGGGGGGGGGGGGCGCGCGCCAGGCGGGGCGGGGCGGGGCGAGGGGC

GGGGCGGGGCGAGGCGGAGAGGTGCGGCGGCAGCCAATCAGAGCGGCGCGCTCCG

AAAGTTTCCTTTTATGGCGAGGCGGCGGCGGCGGCGGCCCTATAAAAAGCGAAGCG

CGCGGCGGGCGGGAGTCGCTGCGCGCTGCCTTCGCCCCGTGCCCCGCTCCGCCGCCG

CCTCGCGCCGCCCGCCCCGGCTCTGACTGACCGCGTTACTAAAACAGGTAAGTCCGG

CCTCCGCGCCGGGTTTTGGCGCCTCCCGCGGGCGCCCCCCTCCTCACGCGCGAGCGCT

GCCACGTCAGACGAAGGGCGCAGCGAGCGTCCTGATCCTTCCGCCCGGACGCTCAG

GACAGCGGCCCGCTGCTCATAAGACTCGGCCTTAGAACCCCAGTATCAGCAGAAGG

ACATTTTAGGACGGGACTTGGGTGACTCTAGGGCACTGGTTTTCTTTCCAGAGAGCG

GAACAGGCGAGGAAAAGTAGTCCCTTCTCGGCGATTCTGCGGAGGGATCTCCGTGG

GGCGGTGAACGCCGATGATGCCTCTACTAACCATGTTCATGTTTTCTTTTTTTTTCTA

CAGGTCCTGGGTGACGAACAGGGTACCGCCACCATGAGGGGCATGAAGCTGCTGGG
```

-continued

```
GGCGCTGCTGGCACTGGCGGCCCTACTGCAGGGGGCCGTGTCCATGGCGTGCCTGG

GCTTTCAGCGCCATAAAGCGCAGCTGAACCTGGCGACCCGCACCTGGCCGTGCACC

CTGCTGTTTTTTCTGCTGTTTATTCCGGTGTTTTGCAAAGCGATGCATGTGGCGCAGC

CGGCGGTGGTGCTGGCGAGCAGCCGCGGCATTGCGAGCTTTGTGTGCGAATATGCG

AGCCCGGGCAAAGCGACCGAAGTGCGCGTGACCGTGCTGCGCCAGGCGGATAGCCA

GGTGACCGAAGTGTGCGCGGCGACCTATATGATGGGCAACGAACTGACCTTTCTGG

ATGATAGCATTTGCACCGGCACCAGCAGCGGCAACCAGGTGAACCTGACCATTCAG

GGCCTGCGCGCGATGGATACCGGCCTGTATATTTGCAAAGTGGAACTGATGTATCCG

CCGCCGTATTATCTGGGCATTGGCAACGGCACCCAGATTTATGTGATTGATCCGGAA

CCGTGCCCGGATAGCGATTTTCTGCTGTGGATTCTGGCGGCGGTGAGCAGCGGCCTG

TTTTTTTATAGCTTTCTGCTGACCGCGGTGAGCCTGAGCAAAATGCTGAAAAAACGC

AGCCCGCTGACCACCGGCGTGTATGTGAAAATGCCGCCGACCGAACCGGAATGCGA

AAAACAGTTTCAGCCGTATTTTATTCCGATTAACTTCTAGAAT

3'
```

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the mRNA expression cassette sequences is not necessary in order to have the desired result of increased biosynthesis of the target biomolecule as a result of the target cell producing mRNA of the target biomolecule. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Example 1—Expression Cassette

Expression cassettes for expressing mRNA were synthesized. The synthesized mRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified and the bands on interest were also excised and purified using a gel extraction kit. These PCR products contained the mRNA expression cassettes in addition to 15 base pair 5' and 3' overhangs that aligned with the ends of the linearized pAVA-00200 backbone. Using in-fusion cloning, the amplified mRNA expression cassettes are integrated with the pAVA-00200 backbone via homologous recombination. The resulting RP contained the following: 5' ITR, CASI promoter, mRNA expression cassette, WPRE, SV40 polyA and ITR 3'.

The invention claimed is:

1. A composition that comprises a recombinant plasmid (RP) comprising a sequence of-nucleotides that encodes a messenger ribonucleic acid (mRNA) that encodes a precursor protein, wherein the precursor protein is encoded by SEQ ID NO. 2.

2. The composition of claim 1, wherein the sequence of nucleotides is inserted within a protein coat, a lipid vesicle, or any combination thereof.

3. The composition of claim 1, wherein the sequence of nucleotides is inserted within in a viral vector.

4. The composition of claim 3, wherein the viral vector is one of a double stranded DNA virus, a single stranded DNA virus, a single stranded RNA virus, or a double stranded RNA virus.

5. The composition of claim 3, wherein the viral vector is an adeno-associated virus.

6. The composition of claim 1, wherein the precursor protein is a precursor of Cytotoxic T-Lymphocyte Associated Protein 4 (CTLA-4).

7. A composition that comprises a recombinant plasmid (RP) with a sequence of nucleotides that encodes a sequence of messenger ribonucleic acid (mRNA) that encodes a precursor protein, wherein the sequence of nucleotides is SEQ ID NO. 3.

* * * * *